United States Patent

Closmann et al.

[11] Patent Number: 4,480,039
[45] Date of Patent: Oct. 30, 1984

[54] HEAVY OIL SAMPLE PREPARATION

[75] Inventors: Philip J. Closmann, Houston; James T. Wortham, Edna, both of Tex.

[73] Assignee: Shell Oil Company, Houston, Tex.

[21] Appl. No.: 448,542

[22] Filed: Dec. 10, 1982

[51] Int. Cl.³ .................. G01N 1/00; G01N 33/28; C10M 11/00

[52] U.S. Cl. .................. 436/175; 208/88; 208/184; 208/186; 436/177; 436/178

[58] Field of Search .............. 203/47, 73, 91; 208/88, 208/184, 186, 251 R; 436/25, 29, 174, 175, 177, 178

[56] References Cited

U.S. PATENT DOCUMENTS

| | | | |
|---|---|---|---|
| 1,838,718 | 12/1931 | Stutler | 208/184 |
| 2,239,470 | 4/1941 | Schick | 203/91 X |
| 2,906,693 | 9/1959 | Donaldson | 208/251 R |
| 3,791,965 | 2/1974 | Fitzsimmons et al. | 208/184 X |
| 4,073,720 | 2/1978 | Whisman et al. | 208/184 X |
| 4,233,140 | 11/1980 | Antonelli et al. | 208/184 X |
| 4,263,102 | 4/1981 | Schorr et al. | 203/73 X |
| 4,399,252 | 8/1983 | Cunningham | 208/184 X |

FOREIGN PATENT DOCUMENTS 0442081 1/1936 United Kingdom .............. 208/186

Primary Examiner—Arnold Turk
Assistant Examiner—Robert J. Hill, Jr.

[57] ABSTRACT

A substantially solids-free sample of an oil having substantially the same hydrocarbon distribution as a heavy oil contained in a subterranean reservoir is prepared by vacuum-topping a field sample of the oil or oil-containing material while cold-trapping volatiles, diluting the topped oil with a volatile oil solvent, mechanically separating the solution from entrained solids, vacuum-distilling the solvent from the dissolved oil and recombining the oil and the cold-trapped volatiles.

3 Claims, 2 Drawing Figures

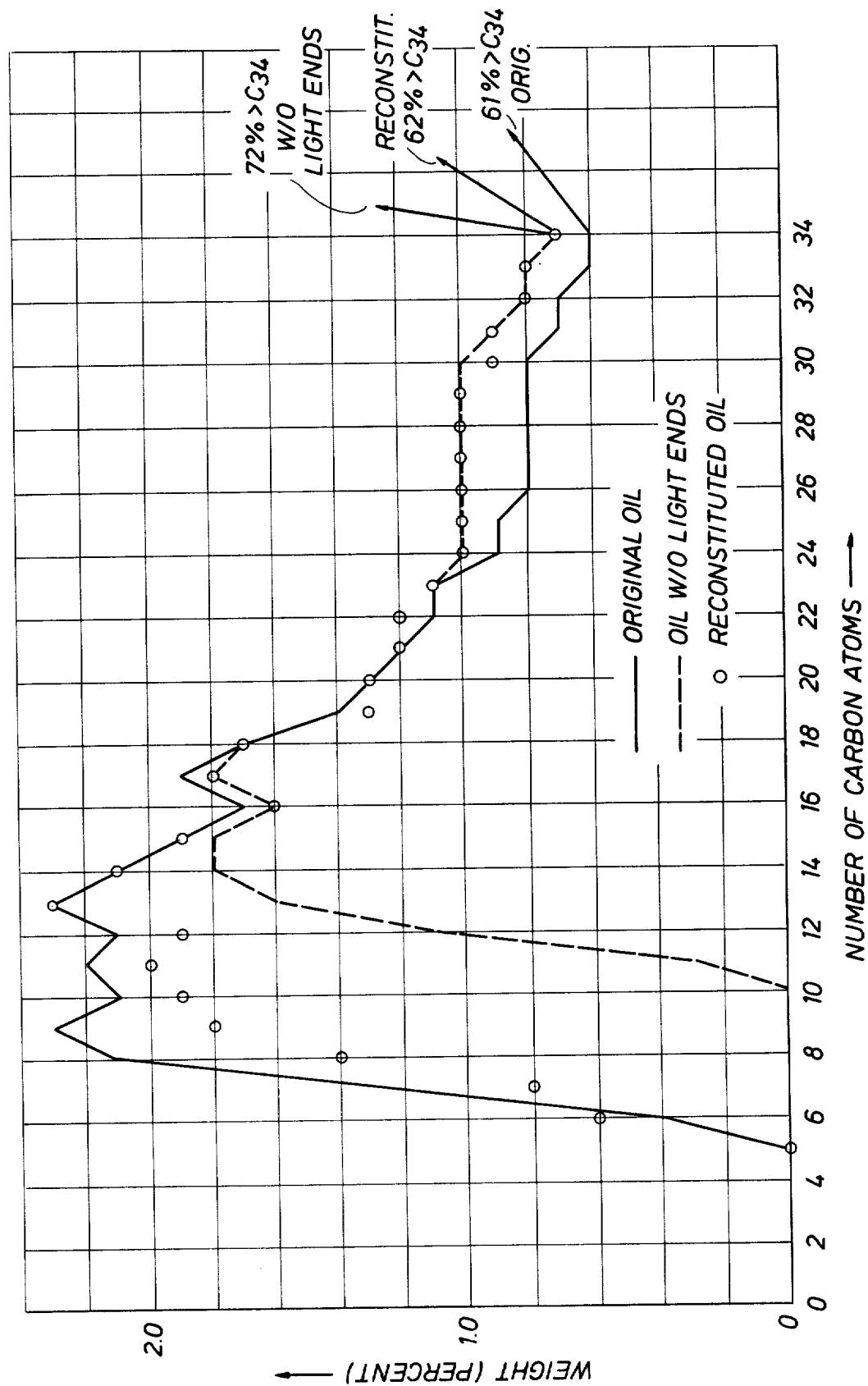

4,480,039

HEAVY OIL SAMPLE PREPARATION

BACKGROUND OF THE INVENTION

This invention relates to extracting a heavy oil from a field sample of the oil and/or oil-containing portion of a subterranean oil formation and preparing a substantially solids-free oil sample having a chemical composition which is substantially identical to that of the oil in the reservoir.

As far as applicants have been able to ascertain, the methods of separating such oils from field samples and preparing samples for laboratory utilizations have remained substantially the same for at lest about 40 years. For example, the textbook "Petroleum Production Engineering Oil Field Development" by Lester Charles Uren, McGraw-Hill Book Company, Inc., 1946, describes a procedure for extracting oil from field samples. It comprises contacting the sample in a Soxhlet extractor with substantially any volatile solvent which does not alter the mineral structure of the reservoir material and is capable of dissolving the oil or oil residue from the reservoir material. In a booklet, "Syncrude Analytical Methods for Oil Sand and Bitumen Processing", published by Syncrude Canada, Ltd., August, 1979, the extraction procedure is substantially the same—"The sample is separated into bitumen, water and solids by refluxing with toluene in a solids extraction apparatus. Condensed solid and co-distilled water are continuously separated in a trap, the water being retained in the graduated section" (page 46).

Such prior procedures are relatively widely used but have a serious defect. It is generally desirable to mechanically separate the laboratory sample of the oil from solid particles large than about 0.1 micron; for example, by filtration through a millipore filter or by means of centrifugation. Due to the high viscosity of heavy oils, their dilution with the volatile solvent is usually required. After separating the solid particles, the solvent is removed by evaporation. The evaporation removes most of the water which is present in the original oil and also removes most or all of the volatile components that were present in the oil. Thus, in such prior procedures, the light ends are irretrievably lost and the hydrocarbon distribution within the solids-free sample of the oil is different from that in the original oil. These differences are particularly important in tests of the mobility of the oil in cores or packs at different temperatures and/or in contact with different fluids.

SUMMARY OF THE INVENTION

The present invention relates to a process for preparing a substantially solids-free sample of a heavy oil obtaiined from a subterranean reservoir formation so that the hydrocarbon distribution in the solids-free oil is substantially the same as that in the reservoir oil. As a first step, the volatile hydrocarbon components are vacuum-distilled from a field sample of oil or oil-containing material from the subterranean reservoir formation. The distillation is conducted at a temperature which is greater than the boiling point of the oil solvent to be used but less than the boiling or cracking temperature of the heavy hydrocarbon components of the reservoir oil. Substantially all of the distilled light ends and water are condensed and retained. Water is mechanically separated from the condensed volatile hydrocarbon components. The "topped" heavy hydrocarbon components of the reservoir oil, which remain as a distillation residue, are dissolved in a volatile oil solvent and the solution is mechanically separated from substantially all solid particles having diameters greater than about 0.1 micron. Subtantially all of the oil solvent is then vacuum-distilled from the solids-free solution of the heavy hydrocarbon components of the reservoir oil. The condensed volatile hydrocarbon components of the reservoir oil are then combined with the solids-free heavy hydrocarbons, remaining as a residue from the distillation of the solvent, in order to form a reconstituted solids-free reservoir oil having substantially the same hydrocarbon distribution as the oil in the reservoir.

DESCRIPTION OF THE DRAWING

FIG. 2 is a graph of the weight percent of hydrocarbons with the indicated numbers of carbon atoms.

DESCRIPTION OF PREFERRED EMBOIDMENTS

Figure 1:
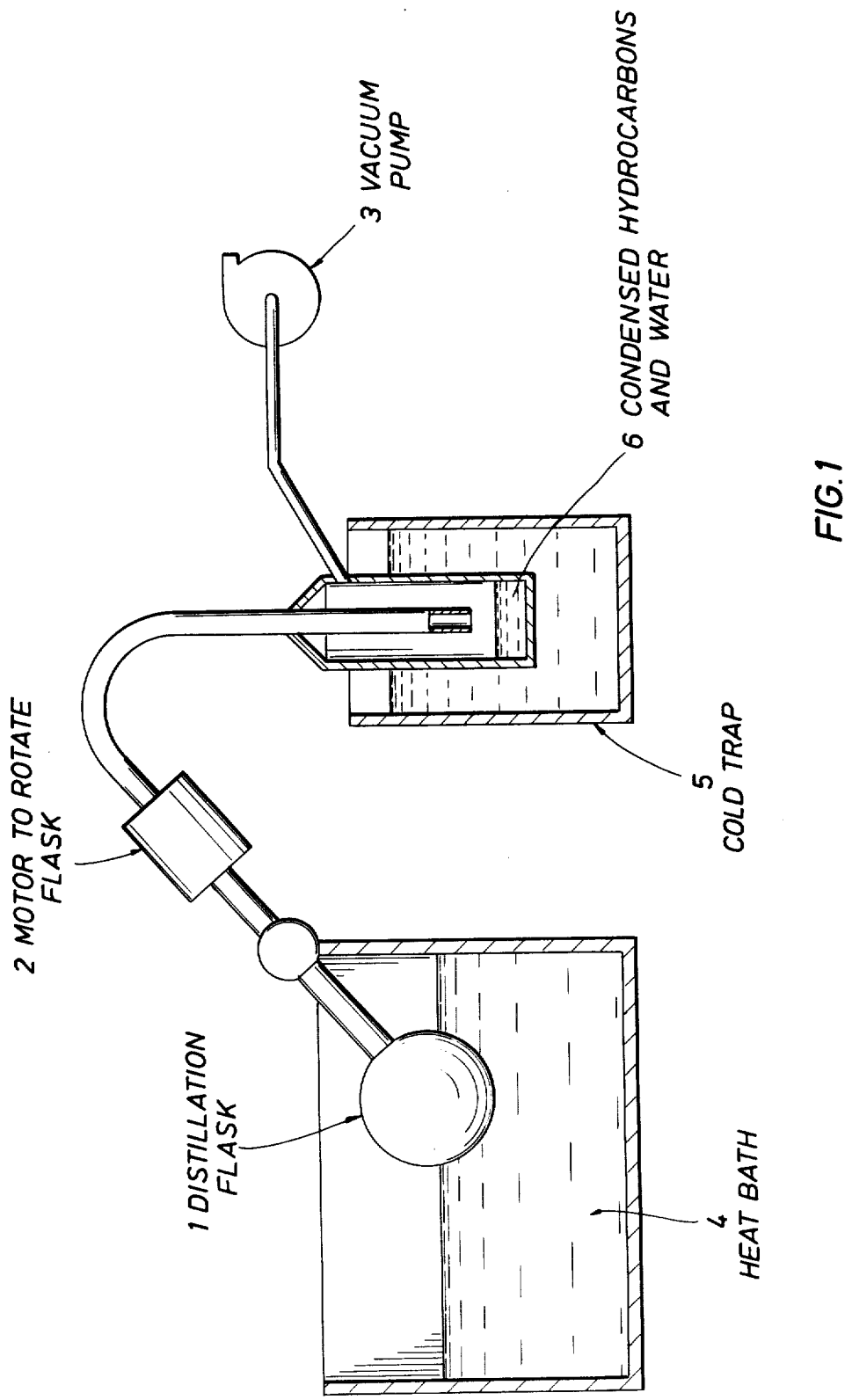
FIG. 1 is a schematic illustration of an apparatus suitable for vacuum-distilling the volatile components from a reservoir oil in accordance with the present invention.

FIG. 1 shows an apparatus with which the volatile hydrocarbon components or light ends can advantageously be vacuum-distilled from a field sample of the reservoir oil or an oil-containing portion of the subterranean reservoir formation. The field sample is placed in distillation flask 1, which is arranged to be mechanically rotated by a motor unit 2 while being evacuated by a vacuum pump 3. The distillation flask is preferably heated in a liquid-filled fluid bath 4. The volatilized light ends and any water present in the field sample are preferably condensed in an evacuated container immersed in a liquid-filled cold trap 5. Such a cold trap is preferably cooled by liquid nitrogen, a mixture of acetone and dry ice, or the like, to form a condensed liquid 6 comprising condensed "light" or volatile hydrocarbons and any water that was present in the field sample.

The initial evacuation or distillation of the volatile hydrocarbon and water components of the field sample can conveniently be conducted in a distillation flask connected to a stirring and evacuating system such as a Rotovac Unit available from Buchlar Instruments. Such a vacuum distillation is preferably conducted at a relatively "hard vacuum" at least as low as about 0.01 millimeter of mercury. The distillation flask is preferably heated in a water bath to a temperature of not more than about 70° C. Where the field sample is, or contains, portions of solid reservoir formation material, that solid material is preferably crushed and placed in the distillation flask along with heat transfer-material such as relatively large steel balls.

After the vacuum-distillation of the volatile components of the field sample, the residual material in the distillation flask is contacted with a volatile oil solvent and dissolved and/or dispersed to form a solution containing substantially all of the heavy hydrocarbon components of reservoir oil. The volatile oil solvent preferably comprises at least one liquid which is substantially completely miscible with substantially all components of the reservoir oil and contains non-hydrocarbon groups or atoms and/or radioactive isotopes which are readiliy detectable in the presence of hydrocarbons, for making it easy to detect the amount of the solvent which is mixed with hydrocarbon components of the reservoir oil. Halogenated hydrocarbon oil solvents such as methylene chloride, chloroform, Freon-11(b.p. about 24° C.) and mixtures such as methanol and chloroform are suitable. Methylene chloride is a particularly suitable solvent.

The resulting solution of heavy oil hydrocarbons in an oil solvent is mechanically freed of solid particles by a mechanical means such as filtration or centrifugation. The separation is preferably accomplished by filtering the solution through a millipore filter having pore sizes of about 0.1 micron. Such a separation can be conducted by means of substantially any of the conventionally available methods or apparatuses.

The volatile oil solvent in the resulting substantially solids-free solution of heavy hydrocarbons is preferably distilled out of that solution (for example, at a temperature no greater than about 50° C. in the case of methylene chloride solvent) to an extent reducing the solvent concentration in the solution to less than about 0.1 percent by weight. In general, the temperature at which the volatile oil solvent is distilled should be at least about 10° C. less than the temperature at which the volatile components were distilled from the field sample. The heavy hydrocarbons remaining after the distillation of the volatile oil solvent are then mixed with the volatile hydrocarbons condensed in the initial vacuum-distillation of the field sample to provide a substantially solids-free sample of a reservoir oil having a hydrocarbon distribution substantially equalling that of the oil in the reservoir.

EXAMPLES:

The following example illustrates a reconstruction of the original hydrocarbon distribution of a sample of Cat Canyon crude oil by means of an initial evacuation, cold-tapping and recombination in accordance with the present process. The hydrocarbon distributions at each stage are shown in Table 1. As known to those skilled in the art the exemplified results would be substantially unchanged by the inclusion of the presently specified procedures of diluting the initially evacuated, mechanically removing solids, distilling of the solvent prior to the recombining of the light and heavy components as exemplified.

The hydrocarbon distributions were obtained by a standard "simulated boiling point" procedure. In that procedure a relatively small sample in stripped with inert gas at a relatively high temperature and the residue is burned while measurements are being made of the proportions of each of the hydrocarbon fractions. The results have a known correlation with the hydrocarbon distribution that would be obtained by an actual distillation of a relatively large sample.

TABLE 1

| Carbon Number | B.P., °C. at 760 mm | Volatility Distribution, Weight Percent | | |
|---|---|---|---|---|
| | | Column A | Column B | Column C |
| 4 | −0.5 | — | — | — |
| 5 | 36.1 | — | — | — |
| 6 | 68.7 | 0.4 | 0.0 | 0.6 |
| 7 | 98.4 | 1.3 | 0.0 | 0.8 |
| 8 | 125.7 | 2.1 | 0.0 | 1.4 |
| 9 | 150.8 | 2.3 | 0.0 | 1.8 |
| 10 | 174.1 | 2.1 | 0.0 | 1.9 |
| 11 | 195.9 | 2.2 | 0.3 | 2.0 |
| 12 | 216.3 | 2.1 | 1.1 | 1.9 |
| 13 | 235.4 | 2.3 | 1.6 | 2.3 |
| 14 | 253.6 | 2.1 | 1.8 | 2.1 |
| 15 | 270.6 | 1.9 | 1.8 | 1.9 |
| 16 | 286.8 | 1.7 | 1.6 | 1.6 |

TABLE 1-continued

| Carbon Number | B.P., °C. at 760 mm | Volatility Distribution, Weight Percent | | |
|---|---|---|---|---|
| | | Column A | Column B | Column C |
| 17 | 301.8 | 1.9 | 1.8 | 1.8 |
| 18 | 316.1 | 1.7 | 1.7 | 1.7 |
| 19 | 329.7 | 1.4 | 1.4 | 1.3 |
| 20 | 342.7 | 1.3 | 1.3 | 1.3 |
| 21 | 355.6 | 1.2 | 1.2 | 1.2 |
| 22 | 367.6 | 1.1 | 1.1 | 1.2 |
| 23 | 379.0 | 1.1 | 1.1 | 1.1 |
| 24 | 389.9 | 0.9 | 1.0 | 1.0 |
| 25 | 400.4 | 0.9 | 1.0 | 1.0 |
| 26 | 410.5 | 0.8 | 1.0 | 1.0 |
| 27 | 420.2 | 0.8 | 1.0 | 1.0 |
| 28 | 429.6 | 0.8 | 1.0 | 1.0 |
| 29 | 438.6 | 0.8 | 1.0 | 1.0 |
| 30 | 447.3 | 0.8 | 1.0 | 0.9 |
| 31 | 456 | 0.7 | 0.9 | 0.9 |
| 32 | 464 | 0.7 | 0.8 | 0.8 |
| 33 | 472 | 0.6 | 0.8 | 0.8 |
| 34 | 479 | 0.6 | 0.7 | 0.7 |
| >34 | >479 | 61. | 72. | 62. |

The hydrocarbon distribution of the original tar is listed in Column A. After that tar was heated and subjected to evacuation at a temperature of about 70° C., its hydrocarbon distribution was that shown in Column B. When the volatile hydrocarbon components were recovered from the cold trap and added back to the topped tar sample (having the composition shown in Column B) the composition of the reconstituted tar is shown in Column C.

The tabulated results show that in the topped sample the C7 and C8 components are substantially missing and there is a significant increase in the fraction of components heavier than C34. Such an increase is typically produced by a loss of light ends. Column C shows that the adding back of the cold-trapped volatiles substantially reproduces the original hydrocarbon distribution of the original sample.

FIG. 2 shows a graph of the results listed in Table 1. In the exemplified procedure the volatile hydrocarbon components cold trapped at the temperature of an acetone/dry ice bath. As shown in FIG. 2, the volatility distribution is completely different for the original and that oil after the light ends were removed, up to carbon numbers of about 15. The reconstituted oil, however, has most of the missing fractions. It is possible that, even with the procedure exemplified, a trace of light ends can be lost. This could be minimized by using a liquid nitrogen cold trap or other trap of lower temperature.

To illustrate the effect of the light ends on the overall viscosity, it should be noted that a crude such as that shown in FIG. 2 would have a viscosity of about 2300 centipoises at 75° F. If about 12% of the light ends are lost due to an inadequate condensation of the initially vaporized light ends (as discussed above and indicated in FIG. 2), and/or due to vaporization with solvent removal, the residue would probably have a viscosity of at least 9000 centipoises. Such a marked difference in viscosity could considerably affect the flow properties of the recovered material.

Such viscosity differences may be important. Although different crude oils are sometimes considered to be similar if their API gravities are similar (and thus may be expected to have similar flow properties) there is surprisingly little correlation between a high API gravity and a low viscosity. A plot showing the trend of API gravity with oil viscosity is given in "Laboratory Test on Heavy Oil Recovery by Steam Injection", SPE Paper No. 10778, presented at the 1982 California Regional Meeting of SPE, Mar. 24–26, 1982, by P. J. Closmann and R. D. Seba.

What is claimed is:

1. A process for preparing for laboratory utilizations a substantially solids-free sample of a heavy reservoir oil in which the hydrocarbon distribution is substantially the same as that in the reservoir oil, comprising:

vacuum-distilling volatile components from a field sample of oil or oil-containing material from a subterranean heavy oil reservoir at a temperature which is at least significantly greater than the boiling point of an oil solvent to be used for subsequently dissolving the heavy hydrocarbon components of the reservoir oil but is less than the boiling or cracking temperature of the heavy hydrocarbon components of the reservoir oil while condensing and retaining substantially all of the distillate;

mechanically separating water from hydrocarbon components of the resultant condensate;

dissolving the remaining topped heavy hydrocarbon components of the reservoir oil in a volatile oil solvent and mechanically freeing the solution of substantially all solid particles having diameters greater than about 0.1 micron;

distilling substantially all of the volatile oil solvent from the solids-free solution at a temperature and pressure which is significantly less than that used in the vacuum distillation of the field sample; and combining the condensed volatile hydrocarbon components with the heavy hydrocarbon components from which solids have been removed to provide a substantially solids-free sample of oil having a hydrocarbon distribution substantially equalling that of the reservoir oil.

2. The process of claim 1 in which the vacuum distillation of volatile hydrocarbon components is conducted at a temperature of about 70° C. and a pressure of less than about 0.01 millimeter of mercury and the volatile oil solvent in which the topped heavy hydrocarbon components of the reservoir oil are dissolved contains at least one non-hydrocarbon group or atom and is distilled from the solution at a temperature less than about 60° C.

3. The process of claim 2 in which the volatile oil solvent is methylene chloride and is distilled from the solution at about 50° C.

* * * * *